United States Patent [19]
Bachand

[11] Patent Number: 6,010,663
[45] Date of Patent: Jan. 4, 2000

[54] DIE CUT REAGENT MEMBRANE, HOLDER

[75] Inventor: Steven S. Bachand, Laguna Niguel, Calif.

[73] Assignee: Ansys, Inc., Irvine, Calif.

[21] Appl. No.: 08/855,026

[22] Filed: May 13, 1997

[51] Int. Cl.$^7$ .................................................. G01N 21/00
[52] U.S. Cl. ............................ 422/58; 422/57; 422/104; 435/805; 436/518; 156/178
[58] Field of Search .............................. 436/518; 422/57, 422/58, 104; 435/805; 156/178

[56] References Cited

U.S. PATENT DOCUMENTS

| | | | |
|---|---|---|---|
| 4,055,394 | 10/1977 | Friedman et al. | 23/253 TP |
| 4,459,360 | 7/1984 | Marinkouich | 436/513 |
| 4,518,565 | 5/1985 | Boger et al. | 422/58 |
| 4,595,439 | 6/1986 | Boger et al. | 156/78 |
| 4,673,657 | 6/1987 | Christian | 436/501 |
| 4,774,192 | 9/1988 | Terminiello et al. | 436/530 |
| 4,789,629 | 12/1988 | Baker et al. | 435/7 |
| 4,803,170 | 2/1989 | Stanton et al. | 436/518 |
| 4,963,325 | 10/1990 | Lennon et al. | 422/61 |
| 5,240,844 | 8/1993 | Wie et al. | 435/7.92 |
| 5,501,837 | 3/1996 | Sayles | 422/58 |
| 5,571,667 | 11/1996 | Chu et al. | 435/5 |

*Primary Examiner*—Christopher L. Chin
*Assistant Examiner*—Jennifer Graser
*Attorney, Agent, or Firm*—Walter A. Hackler

[57] ABSTRACT

An assaying device and a method of manufacturing same are provided. The assaying device includes a unitary, absorbent membrane having multiple reagent stripes incorporated therein. The reagent stripes display an observable reaction if a sample component is present in a fluid sample being tested. The reagent stripes are deposited simultaneously on a continuous membrane ribbon and individual membranes are die cut therefrom. Each individual membrane includes commonly connected channels having die cut slots therebetween. The channels are preferably disposed perpendicularly with respect to the reagent stripes and provide means for causing contact between the fluid and reagent stripes. The present invention preferably includes a cassette for containing the membrane and for facilitating analysis of test results. During assembly of an assaying device, the unitary membrane is easily inserted into the cassette by engaging the slots with ridges in the cassette, thus minimizing a chance of error of alignment of the channels. The present invention is suitable for multiple component qualitative analysis as well as semi-quantitative analysis.

9 Claims, 2 Drawing Sheets

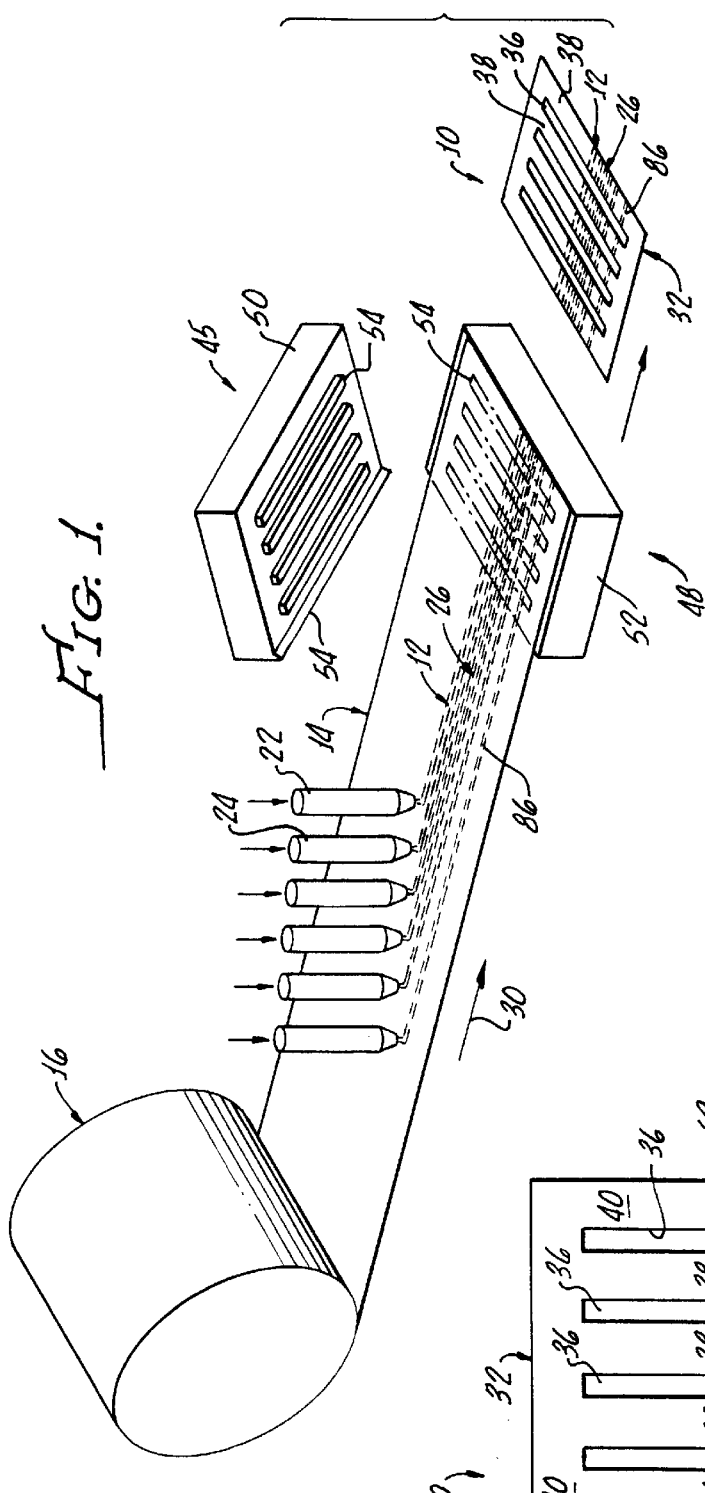

DIE CUT REAGENT MEMBRANE, HOLDER

The present invention is directed to a device for detecting the presence of substances in a fluid sample and more specifically to an assay kit for qualitative and semi-quantitative analysis of fluid sample and a method for manufacturing same.

Devices for testing for the presence of single or multiple substances in a single fluid sample are well known. The demand for inexpensive, accurate and simple to use devices for testing, or assaying, biological specimens has increased in recent years in both medical and non-medical settings. For example, in a hospital where patients are subjected to massive dosages of antibiotics, a small amount of blood may be withdrawn from the patient and the serum assayed for determining an if an appropriate amount of antibiotic is present in the blood. As another example, in a hospital emergency room where an overdose patient has impaired cognitive function, or is a small child unable to communicate, the type of drug overdosed must be quickly determined in order to ensure correct administration of treatment. Nonmedical uses of assaying methods and devices include testing of the general population by employers, government agencies, sports groups and other organizations for employment and maintenance of safety in the workplace. Because of increasingly large numbers of persons being tested, there is a strong need for inexpensive, easy to use and reliable test devices.

Reagent test devices have been developed which generally include an absorbent membrane having incorporated therein a specific reagent which manifests a detectable response, for example a color change, in the presence of a specific component of a sample fluid that is absorbed by the membrane.

Many such test devices for detecting body fluid components are capable of making not only qualitative, but also quantitative or semi-quantitative measurements. Thus, by observing a color change response after a certain period of time, an analyst can obtain not only a positive indication of the presence of a specific component, but also an estimate of how much of the component is present in the sample.

One method for semi-quantitative analysis of a sample involves the uses of tags or marker agents in addition to the component specific reagent. Generally, a known amount of a marker agent is combined with a fluid sample in order to enable the sample component in question to bind with the marker agent, if the component is present in the sample. After the marker agent has become saturated with the component, any uncombined component remaining in the sample, i.e. the portion not bound to the marker, may cause a detectable response in the component specific reagent. Thus, by using known amounts of a marker agent, a relative amount of a sample component can be determined.

Conventionally, many test devices for determining multiple, distinct components of a sample fluid, or for performing semi-quantitative analysis utilize multiple test strips or filaments, each being impregnated or coated with the specific reagent. During assembly of the assaying kit, the separate strips are aligned in a common holder or container. A reservoir in the container is used to hold a fluid sample, and the reservoir and strips are so arranged such that each of the strips will absorb some of the fluid sample.

Although inexpensive materials may be used in the manufacture of conventional assaying devices, such devices require individual alignment and fastening of multiple, separate strips into a holder. The need for handling of a number of individual strips substantially adds to manufacturing time and cost. Moreover, the chance for inaccuracy of test results increases with increased number of strips, as strips may become lost, damaged or misaligned during the assembly process.

The present invention provides a device for testing of multiple substances in a single fluid sample, which is reliable and inexpensive to manufacture because it includes a single, unitary membrane having a number of commonly connected channels with multiple reagents disposed thereon.

SUMMARY OF THE INVENTION

The present invention provides an assaying device, and method for making same, which generally comprises a unitary, integral membrane made of a material capable of absorbing a fluid sample, said membrane including a plurality of die cut slots therein which define multiple, commonly connected, absorbent membrane channels.

Assaying means for indicating a presence of at least one component of the fluid sample is provided. The assaying means comprises one or more capture zones, disposed, for example, in a band or stripe fashion across the membrane. Each capture zone includes a particular reagent therein. The reagent may comprise any suitable composition known in the art which will provide a detectable response in the presence of the component in question. For example, the reagent may be a drug conjugate for detecting the presence of an illicit drug in a body fluid sample.

Preferably, the capture zone stripe is disposed on the membrane generally perpendicularly to the die cut slots and channels. As will be discussed in detail hereinafter, the present invention may include a plurality of said capture zones which have been simultaneously striped onto the membrane, each being generally parallel to one another and each containing a reagent for detecting a particular component of the sample.

Alternatively, or in addition to, the multiple capture zones, means for enabling semi-quantitative analysis may be provided such that a relative amount of a component in the sample may be determined. For example, the assaying means may additionally comprise a plurality of marker zones, disposed on an upstream end of the absorbent channels, each marker zone including a different concentration of a particular signal carrying agent. Each channel is then useful for measuring for the presence of a predetermined minimum level of component in the fluid sample.

In the semi-quantitative analysis embodiment, the slots between the charnels function in part to prevent mixing of conjugates in one channel with conjugates in an adjacent channel, thus preserving integrity of test results.

Preferably, the slots are die cut into the membrane such that the slots are disposed inside a perimeter of the membrane such that the perimeter is comprised of a continuous common area about the die cut slots.

The present invention preferably includes a rigid holder for containing the unitary membrane and enabling hygienic handling thereof. The holder may be a cassette comprised of a cover portion and a base portion with the base portion including interior projections for engaging the slots and accurately aligning the membrane. The top portion of the cassette includes apertures therein for receiving the fluid sample and windows for enabling observation of capture zones when the membrane is enclosed between the cover and base. In addition, the cassette cover may include grooves for receiving the base projections, thus providing a fluid tight fitting between adjacent channels and preventing shifting or misalignment of the membrane.

The method of the present invention generally includes the steps of striping a continuous membrane ribbon with single or multiple reagents, for example, drug conjugates in the case of drug testing, and die cutting individual unitary membranes, each having multiple channels, therefrom. The die cutting step includes the step of cutting slots into each membrane to define the channels, the slots and channels being disposed perpendicular to the striped reagents. The unitary membrane is inserted into a cassette having interior projections for engaging the slots and aligning the membrane with the windows in the cassette for enabling observation of the capture zones.

BRIEF DESCRIPTION OF THE DRAWINGS

The advantages and features of the present invention will be better understood with the following detailed description when considered in conjunction with the accompanying drawings of which:

FIG. 1 is a representation of a method of the present invention for manufacturing an assaying device, as well as an assaying device manufactured by such a method;

FIG. 2 shows an assaying device in accordance with the present invention, comprising a unitary membrane having die cut slots defining channels, and capture zones striped perpendicular thereto;

DETAILED DESCRIPTION

Figures 3, 4:
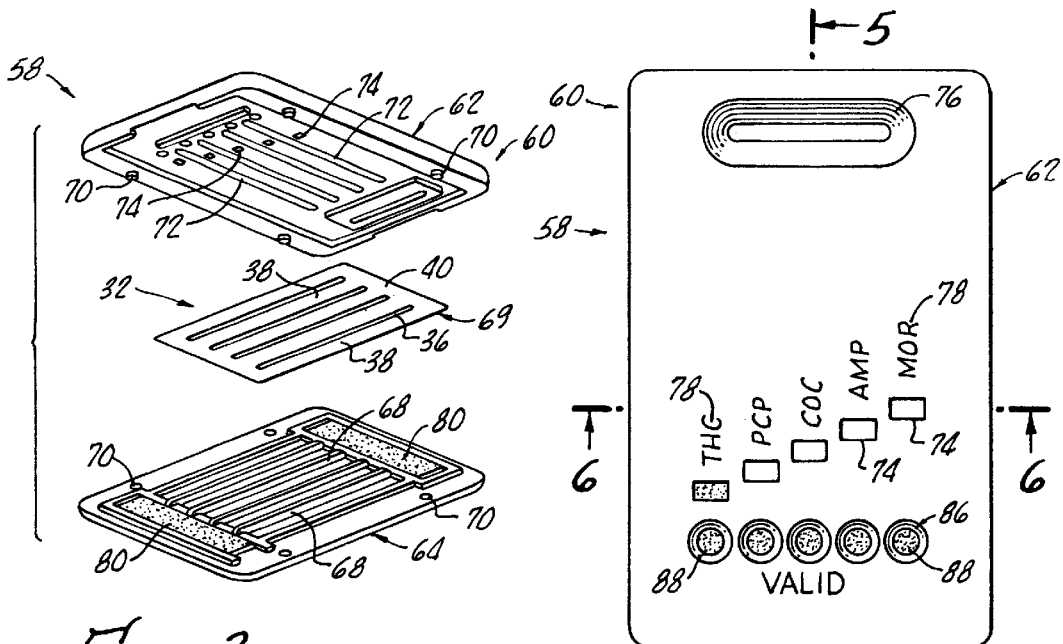
FIG. 3 shows an exploded view of another embodiment of the present invention having a membrane as well as a cassette for containing the membrane.
FIG. 4 shows a top plan view of an embodiment of the present invention useful for qualitative drug testing of a fluid sample.

Turning now to FIGS. 1 and 2, an assaying device 10 in accordance with the present invention and a representation of a method for manufacturing same is shown.

More particularly, a method for manufacturing the assaying device 10 generally comprises the step of first depositing at least one reagent stripe 12, on a continuous membrane ribbon 14 made of a material capable of absorbing a fluid sample (not shown). For example, the membrane ribbon 14 may comprise a suitable absorbent paper. The continuous membrane ribbon 14 may be provided as a wound spool 16 of such material.

The reagent stripe 12 may be comprised of any of the many well known reagents 22 capable of causing an observable reaction, for example a color change, in the presence of a specific component of the fluid sample, and will be specific to the type of component being tested. As examples, the reagent may be comprised of a drug conjugate matching a drug, or antibodies matching antigens, that are a subject of the test.

As will be discussed hereinafter, the present invention provides a method for manufacturing an assaying device 10 capable of qualitative analysis of multiple components of a sample. In the embodiment shown in FIGS. 1 and 2, a plurality of different reagents 22, 24, matching the sample components to be detected, are prepared in a conventional fashion and deposited on the ribbon 14 as multiple parallel stripes 12. 26. More particularly, each stripe 12, 26 may be deposited by discharging a particular reagent 22, 24, respectively, onto the ribbon 14 while the ribbon spool 16 is being unrolled and the ribbon 14 conveyed in a direction represented by arrow 30. The reagent stripes 12, 26 are preferably spaced apart form one another such that a reagent-free area 39 of membrane material divides the adjacent reagent stripes 12, 26.

During the step of depositing the reagent stripes 12, 26, or at sometime thereafter, the continuous membrane ribbon 14 is die cut into individual, separate membranes 32, each separate membrane 32 having a portion of the reagent stripe 12, 26 deposited thereon. Importantly, at least one slot, preferably multiple parallel slots 36, are die cut from the membrane 32 in order to obtain a unitary membrane 32 having a plurality of commonly connected absorbent channels 38 disposed adjacent and between the slots 36.

The slots 36 are preferably cut interior to a perimeter 39 of the membrane 32, such as shown, leaving a common area 40 of membrane material about the slots 36. Alternatively, although not shown in the drawings, the slots may be cut such that they form slot openings in a lower edge of the membrane 32, creating finger-like channels commonly connected at an upper edge of the membrane 32. Preferably, the slots 36 are die cut parallel with respect to each other and perpendicularly with respect to the reagent stripes 12, 26.

Although a total of four slots 36 and five channels 38 are shown in FIGS. 1 and 2, it should be appreciated that any number of slots 36 and channels 38 may be provided, depending on the assaying to be performed. Furthermore, although a rectangular membrane 32 with parallel slots 36 forming parallel channels 38 is shown, it should be appreciated that the method of the present invention may include die cutting a different shaped unitary membrane from the ribbon 14, for example, a circular membrane having slots disposed in a spoked fashion about a center of the circular membrane.

Once the slots 36 and channels 38 have been formed into the membrane 32, each reagent stripe 12, 26 becomes a divided capture zone 44 across each channel 38 which provides distinct areas of the channel 38 containing the reagent 22, 24 for indicating a presence or absence of the respective components being tested.

Preferably, the step of die cutting the continuous membrane ribbon 14 and the step of die cutting the slots 36 are performed simultaneously by using a conventional die apparatus 48, having dimensions designed for this purpose. For example, the die apparatus 48 may include an upper portion 50 and a lower portion 52 having cooperative cutting blades 54 adapted for cutting apart adjacent membranes 32 and punching slots 36 therein. It should be appreciated that the term "die cut" as used herein is intended to include any method of rapid cutting of sheet material which lends itself to automated production.

Advantageously, the method of the present invention provides an inexpensive method of manufacturing the assaying device 10 shown in the FIG. 2 which can be used for assaying multiple components of a fluid sample without the need for preparing and assembling multiple, individual test strips. As will be discussed hereinafter, the assaying device of the present invention preferably includes a holder, such as a cassette, for supporting the membrane, such as the embodiments shown in FIGS. 3–8.

More particularly, another embodiment 58 of an assaying device in accordance with the present invention is shown in FIG. 3, which generally comprises the unitary membrane 32 having commonly connected channels 38 and capture zones 44 such as shown in FIGS. 1 and 2 and discussed hereinabove, and additionally comprises a cassette 60.

Figure 5:
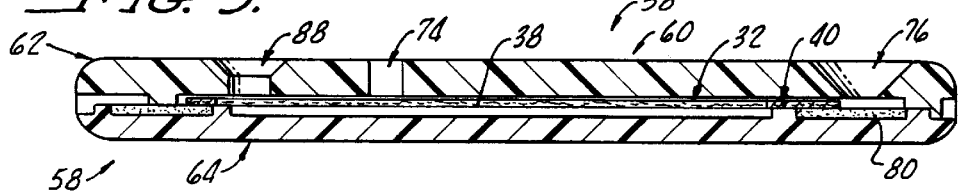
FIG. 5 shows a cross-sectional view of the present invention taken across line 5—5 or FIG. 4.
Figure 6:
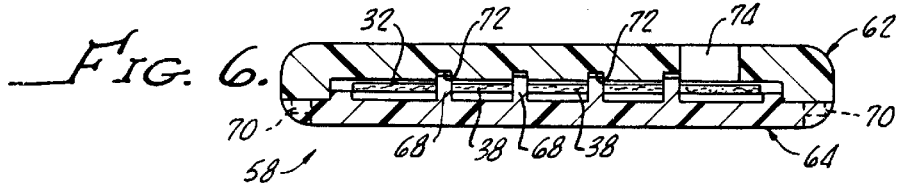
FIG. 6 shows a cross sectional view of the present invention taken across line 6—6 of FIG. 4.

Turning as well to FIGS. 4–6, the cassette 60 may be comprised of a cover 62 and engaging base 64. Importantly, the base 64, or alternatively the cover 62, includes one or more projections 68 for engaging the membrane slots 36 and aligning the membrane 32 within the cassette 60. The projections 68 are preferably the same number and dimension as the slots 36 such that assembly of the assaying device 58 is simple, reliable and leaves minimal opportunity for error.

In the example shown, the membrane 32 includes four slots 36 interior to a perimeter 69 of the membrane 32. Accordingly, the cassette 60 includes four projections 68 having nearly equal dimension as the slots 36.

The assembly of the assaying device 58 is accomplished by simply inserting the membrane 32 into the bottom portion by aligning the slots 36 with the projections 68 and engaging the projections 68 into the slots 36. Next, the cover 62 is caused to engage the base 64 by any suitable means, such as cooperating snap connectors 70.

Additionally, the cassette 60 preferably includes means, such as grooves 72 in the cassette cover 62, for receiving the base projections 68 in order to provide a secure fitting between the base 64 and cover 62 and further prevent shifting or misalignment of the membrane 32. FIGS. 3 and 6. The projection 68 and groove 72 engagement is shown in FIG. 6. The engagement may be fluid tight to prevent fluid communication between adjacent channels 38, the advantages of which will be discussed hereinafter.

As shown, the cassette cover 62 includes apertures, such as windows 74, for revealing a portion of each capture zone 44 and enabling observation thereof, and a relatively larger well 76 for receiving the fluid sample and establishing a fluid communication between the sample and the absorbent membrane 32. The cassette cover 62 preferably includes indicia 78 for indicating a name, or other identification information, of the sample component that will cause an observable reaction in the adjacent window 74.

Importantly, the projections 68 and grooves 72 maintain positive alignment of the membrane within the cassette 60, hence handling or shipping of the cassette 60 will not dislodge or otherwise move the membrane 32 within the cassette 60. This ensures that the assaying device 58 will function properly and will display accurate test results through the windows 74.

In use, a suitable volume of sample fluid, such as blood serum, is deposited into the well 76 of an assembled assaying device 58 in accordance with the present invention. The fluid will saturate the common area 40 of the membrane immediately adjacent the well 76. Absorbent padding 80 may be provided in the base 64 for capturing excess fluid that may have been deposited into the well 76. The fluid will travel through the channels 38 by capillary action due to the absorbent nature of the membrane 32 and eventually reach the capture zones 44 which may change in color, or in some other way indicate a presence or absence of a specific component in the fluid sample.

Advantageously, because of the unity of the channels 38 at the membrane common area 40 disposed immediately adjacent or below the well 76, the sample fluid will tend to migrate into the channels 38 uniformly, such that the fluid will be distributed nearly equally among the several channels 38. Preferably, the well 76 is elongated in shape and equal to a width of the membrane 32. As shown most clearly in FIGS. 4 and 5, the well may have a funnel-shaped cross section to allow a steady flow of fluid into the absorbent membrane 32. The structure of the membrane 32 and the well 76 enhances equality of volume and rate of fluid absorption among the channels 38, thus enhancing accuracy of test results when compared to conventional devices.

Importantly, one particular reagent stripe 86 may be used to indicate a validity of the test, or in-other words, such reagent stripe 86 may operate as a control mechanism to assure that the sample has saturated the channels 38 sufficiently to have contacted each capture zone 44. The control reagent stripe 86 is preferably disposed near a lower, downstream edge of the membrane 32, as shown most clearly in FIGS. 1, 2 and 4. A control window 88 for viewing the control stripe 86 is located downstream of each test window 74 in the cassette cover 62.

Thus, after a sample fluid has been deposited in the well 76 and a sufficient period of time has elapsed to allow for the fluid to migrate through each channel 38, the control windows 88 are observed. If, for example, all of the control windows 88 show a change in color, the test would be considered valid for each test window 74 located upstream of the control windows 88. On the other hand, if a particular control window 88 shows no observable change, then this would indicate the test is invalid in the test window 74 located immediately upstream the particular control window 88. Control reagents suitable for this purpose well known in the art, and thus will not be described hereinafter with more detail.

In the example shown in FIG. 4, the present invention is being used to test for the presence of a variety of drugs in a sample of body fluid. As shown, each control window 88 indicates the test is valid for each drug being tested. Furthermore, the presence of a drug referred to as "THC" has been detected.

Figure 8:
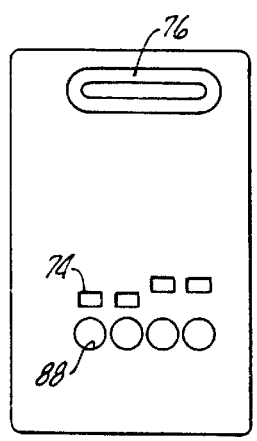
FIG. 8 shows a membrane and cassette in accordance with the present invention suitable for semi-quantitative analysis of multiple components of a fluid sample.
Figure 7:
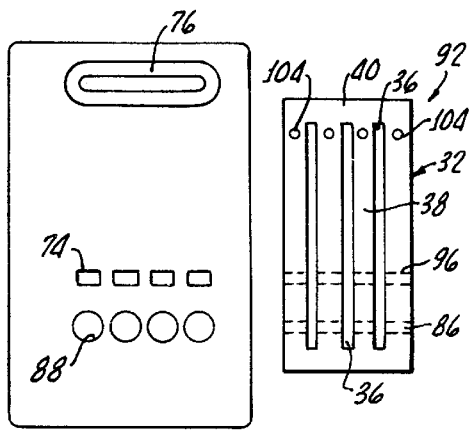
FIG. 7 shows a membrane and a cassette in accordance with the present invention suitable for semi-quantitative analysis of a single component of a fluid sample.

Turning now to FIGS. 7 and 8, alternative embodiments 92, 94 of the present invention are shown suitable for semi-quantitative analysis of a fluid sample such that a relative amount of a component in the sample may be determined.

More particulary, FIG. 7 shows an assaying device 92 in accordance with the present invention useful for semi-quantitative analysis of a single component of a fluid sample, and FIG. 8 shows an assaying device 94 suitable for semi-quantitative analysis of multiple components of a fluid sample. As discussed hereinabove, semi-quantitative analysis is used as a way of determining if a certain minimum amount of a component is present in a fluid sample and thus can be used to determine a relative amount of component present in a sample.

For example, the assaying means may be comprised of a single reagent stripe 96, for single drug semi-quantitative testing, or multiple reagent stripes 98, 100, for multiple drug semi-quantitative testing. Additionally, the assaying means may comprise a plurality of marker zones 104 including signal carrying agents of varying concentrations disposed on an upstream end of the absorbent channels 38. Thus, each particular channel will be used for measuring for the presence of a predetermined minimum level of component in the fluid sample.

The signal carrying agent is preferably unique to the capture zone reagent. Thus, for example, in the embodiment shown in FIG. 7, a semi-quantitative analysis of one component of a sample is to be tested by single reagent stripe 96, using four different concentrations of signal carrying agent, illustrated by different sized marker zones 104. A two component semi-quantitative analysis may be made by the embodiment of Figure 94 using the two different reagent stripes 98, 100, and marker zones 104 comprising two sets of different concentrations of signal carrying agent specific to respective reagent stripes 98, 100.

The signal carrying agent functions to bind with a predetermined amount of the sample component until a saturation point is reached. An observable reaction may occur in a downstream capture zone if an excess amount of component or, alternatively an excess amount of signal carrying agent, is present in the fluid within that particular channel. The signal carrying agent may be particle based, or polymer based technology, or any other suitable technology as known by those skilled in the art.

The marker zones 104 are deposited onto the membrane 32, for example, by spotting the various amounts of signal carrying agent on an upstream end of each channel 38. Preferably, the marker zones 104 are deposited onto each channel at a location immediately downstream of the common area 40 and between the slots 36, to prevent mixing of fluids in adjacent channels 38 during the testing process. Additionally, the channels and the projections function to prevent mixing of the varying amounts of signal carrying agents and sample components during the migration of the fluid by providing a positive barrier between adjacent channels 38. Thus, although the membrane 32 is a unitary structure having commonly connected channels 38, the integrity of the test results displayed in each channel 38 is preserved.

It will be appreciated that the positioning of windows 74 as shown in the three different embodiments 58, 92, 94 facilitates test analysis and enables a quick determination of the type of test the assaying device will be useful for.

Although there has been hereinabove described a die cut reagent membrane, holder and a specific method for manufacturing same, in accordance with the present invention, for the purpose of illustrating the manner in which the invention may be use to advantage, it should be appreciated that the invention is not limited thereto. Accordingly, any and all modifications, variations or equivalent arrangements which may occur to those skilled in the art, should be considered to be within the scope of the present invention as defined in the appended claims.

What is claimed is:

1. An assaying device comprising:
   a cassette having a cover and a base;
   a unitary membrane disposed within the cassette between the cover and the base, said unitary membrane being made of a material capable of absorbing a fluid sample, said unitary membrane including slot means for both creating a plurality of absorbent channels in the membrane and for enabling registration of the membrane within the cassette;
   assaying means, including at least one capture zone disposed on said unitary membrane across each channel, for indicating a presence of at least one specific component of the fluid sample; and
   rib and groove means for registering said unitary membrane within said cassette and for providing a fluid tight engagement between the channels in order to prevent fluid communication between adjacent channels and preserve the integrity of test results displayed in each channel.

2. The assaying device according to claim 1 wherein the capture zones is disposed generally perpendicular to the at least one die cut slot and the cassette cover comprises window means formed in the cassette cover for revealing a portion of each capture zone.

3. The assaying device according to claim 1 wherein the assaying means further includes means, disposed on an upstream end of the absorbent channels, for enabling semi-quantitative analysis of the specific component in the fluid sample.

4. The assaying device according to claim 3 wherein the means for enabling semi-quantitative analysis comprises a plurality of marker zones, each marker zone comprising a different concentration of signal carrying agent.

5. The assaying device according to claim 1 wherein the assaying means includes a plurality of capture zones, each said capture zone including reagent means for detecting a particular component of the fluid sample.

6. The assaying device according to claim 5 wherein the plurality of capture zones are disposed parallel to one another and perpendicular to the slot means.

7. The assaying device according to claim 1 wherein the slot means is disposed interior to a perimeter of the unitary membrane such that a common area of membrane material surrounds the slot means.

8. The assaying device according to claim 1 wherein the cassette cover comprises well means for saturating the membrane, at one end thereof, with the fluid sample.

9. The assaying device according to claim 8 further comprising absorbent padding means, disposed in the cassette base, for capturing excess fluid sample.

* * * * *